(12) United States Patent
Shinbo et al.

(10) Patent No.: US 7,843,570 B2
(45) Date of Patent: Nov. 30, 2010

(54) CRYSTAL OSCILLATOR SENSOR AND SUBSTANCE ADSORPTION DETECTION METHOD USING THE SENSOR

(75) Inventors: Kazunari Shinbo, Niigata (JP); Futao Kaneko, Niigata (JP); Keizo Kato, Niigata (JP); Yasuo Ohdaira, Niigata (JP); Takahiro Kawakami, Niigata (JP)

(73) Assignee: Niigata University, Niigata (JP)

( * ) Notice: Subject to any disclaimer, the term of this patent is extended or adjusted under 35 U.S.C. 154(b) by 329 days.

(21) Appl. No.: 10/591,196

(22) PCT Filed: Jul. 28, 2005

(86) PCT No.: PCT/JP2005/013863

§ 371 (c)(1),
(2), (4) Date: Oct. 1, 2007

(87) PCT Pub. No.: WO2006/038367

PCT Pub. Date: Apr. 13, 2006

(65) Prior Publication Data

US 2008/0060438 A1 Mar. 13, 2008

(30) Foreign Application Priority Data

Oct. 4, 2004 (JP) ............................. 2004-291090

(51) Int. Cl.
*G01N 21/55* (2006.01)
(52) U.S. Cl. .................................... 356/445
(58) Field of Classification Search .................. 422/50, 422/82.05, 82.11; 204/400; 376/245, 248; 356/445–448, 432; 385/12, 17, 30
See application file for complete search history.

(56) References Cited

U.S. PATENT DOCUMENTS 6,408,123 B1 * 6/2002 Kuroda et al. ............... 385/130
2003/0075697 A1 * 4/2003 Ohtsuka et al. ............. 250/573

(Continued)

FOREIGN PATENT DOCUMENTS

JP 05-099827 4/1993

(Continued)

OTHER PUBLICATIONS

Watanabe, et al; "An Optical Fiber Biosensor Based on Anomalous Reflection of Gold"; Elsevier Science; Jun. 19, 2002; pp. 126-130; Tokyo Institute of Technology.

(Continued)

*Primary Examiner*—Tarifur Chowdhury
*Assistant Examiner*—Michael LaPage
(74) *Attorney, Agent, or Firm*—Boyle Fredrickson, S.C.

(57) ABSTRACT

A substance adsorption detection method and a sensor utilizing amounts of change in the optical characteristic of a sensitive thin film with respect to the adsorbed amount of a substance to be detected. A clad 4, a core 5, and a thin film 7 for detecting an adsorbed substance are sequentially stacked on a crystal oscillator 10 to constitute an optical waveguide layer 12 and a gas adsorption member 11. An incoming light prism 8 and an outgoing light prism 9 are provided on the surface of the core 5. Changes in the adsorbed mass of the target substance and in the optical characteristic involved can be detected accurately and simultaneously by utilizing a change in outgoing light originating from a change in propagation loss and a change in the oscillation characteristic of the oscillator 10, both caused by adsorption of the target substance on the core surface.

24 Claims, 2 Drawing Sheets

U.S. PATENT DOCUMENTS

2006/0192955 A1* 8/2006 Jorgenson et al. ............ 356/301
2008/0163688 A1* 7/2008 Wang et al. .................... 73/580

FOREIGN PATENT DOCUMENTS

| JP | 07-043285 | 2/1995 |
| JP | 09-061346 | 3/1997 |
| JP | 2001-108612 | 4/2001 |
| JP | 2002-122600 | 4/2002 |
| JP | 2003-043037 | 2/2003 |
| WO | WO 2006/031198 A1 | 3/2006 |

OTHER PUBLICATIONS

Hunsperger, et al; "Parallel End-butt Coupling for Optical Integrated Circuits"; Applied Optics; vol. 16, No. 4; Apr. 1977; pp. 1026-1032I;.

* cited by examiner

CRYSTAL OSCILLATOR SENSOR AND SUBSTANCE ADSORPTION DETECTION METHOD USING THE SENSOR

TECHNICAL FIELD

The present invention relates to a substance adsorption detection method and a sensor which use a piezoelectric element.

BACKGROUND ART

Known as a conventional adsorption sensor is a sensor capable of detecting a trace of $NO_2$ gas by utilizing a reduction in the oscillation frequency of a crystal oscillator in accordance with the $NO_2$ gas adsorbed on a gas sensitive film as disclosed in Patent Literature 1.

As disclosed in Patent Literature 2, there is known a method of detecting adsorption of a substance by utilizing absorption of an evanescent field, generated by waveguiding light to a waveguide path, by an adsorption substance, and attenuation of the waveguided light.

As disclosed in Patent Literature 3, there is also known a method of depositing a metallic thin film on a waveguide path, utilizing attenuation of waveguided light when a surface plasmon is excited on the metallic thin film by the waveguided light, utilizing a change in the excitation condition of the surface plasmon with adsorption of a substance to be measured, and measuring outgoing light, thereby detecting adsorption of the substance.

Patent Literature 1: Unexamined Japanese Patent Publication No. H7-43285

Patent Literature 2: Unexamined Japanese Patent Publication No. H9-61346

Patent Literature 3: Unexamined Japanese Patent Publication No. 2001-108612

DISCLOSURE OF THE INVENTION

Problems to be Solved by the Invention

While the conventional sensor disclosed in Patent Literature 1 makes it possible to detect a trace of a gas adsorbed on a gas sensitive thin film by utilizing the characteristic of a crystal oscillator, so-called QCM (Quartz Crystal Microbalance), it fails to directly detect the optical characteristics of the substance to be detected and the sensitive thin film after adsorption.

The conventional sensors disclosed in Patent Literatures 2 and 3 have a problem such that the sensors fail to directly detect how much mass of a substance to be detected is adsorbed on an element, and causes a change in outgoing light.

In view of the foregoing problems, it is an object of the present invention to provide a substance adsorption detection method and a sensor which use a piezoelectric element, and ensure simultaneous and accurate detection of the amount of a change in the adsorbed mass of a detection target substance and the amount of a change in an optical characteristic originating therefrom.

Means for Solving the Problems

A substance adsorption detection method according to the first aspect of the invention comprises:

providing an optical waveguide layer which has a clad and a core, said core being made of a higher refractive index medium than said clad, both stacked on a crystal oscillator; and measuring an oscillation characteristic of the crystal oscillator, and light waveguided with the optical waveguide layer serving as an optical waveguide path.

A substance adsorption detection method according to the second aspect of the invention comprises:

constituting a crystal oscillator from a crystal, an electrode formed on one side of said crystal, and an optical waveguide electrode formed on an other side of the crystal and made of a transparent electrically conductive material having a higher refractive index than a refractive index of the crystal; and measuring an oscillation characteristic of the crystal oscillator, and light waveguided with the optical waveguide electrode serving as an optical waveguide path.

A substance adsorption detection method according to the third aspect of the invention comprises:

constituting a crystal oscillator with a crystal and an electrode formed on either side of the crystal; and measuring an oscillation characteristic of the crystal oscillator, and light waveguided with an interior of the crystal oscillator serving as an optical waveguide path.

The substance adsorption detection method is characterized in that a metallic film is formed on the optical waveguide path.

A substance adsorption detection method according to the fourth aspect of the invention comprises:

measuring a propagation characteristic of a surface acoustic wave in a surface acoustic wave element, and light waveguided through an optical waveguide path provided in or on the surface acoustic wave element.

A substance adsorption detection method according to the fifth aspect of the invention comprises:

forming a metallic colloid layer on a crystal oscillator or a surface acoustic wave element;

measuring an adsorbed mass with the crystal oscillator or the surface acoustic wave element; and measuring an optical characteristic of the metallic colloid layer.

The substance adsorption detection method is characterized in that a sensitive material layer whose optical characteristic is changed by substance adsorption is provided.

A sensor according to the sixth aspect of the invention is provided with an optical waveguide layer in which a clad made of a relatively low refractive index medium and a core made of a relatively high refractive index are stacked on a crystal oscillator, and which serves as an optical waveguide path for waveguiding light.

A sensor according to the seventh aspect of the invention has a crystal oscillator that comprises:

a crystal;

an electrode formed on one side of the crystal; and an optical waveguide electrode which is formed on an other side of the crystal, made of a transparent electrically conductive material having a higher refractive index than a refractive index of the crystal, and serves as an optical waveguide path for waveguiding light.

A sensor according to the eighth aspect of the invention constitutes a crystal oscillator with a crystal and an electrode formed on either side of the crystal, and measures an oscillation characteristic of the crystal oscillator, and light waveguided with an interior of the crystal oscillator serving as an optical waveguide path.

The sensor of the invention is characterized in that a metallic film is formed on the optical waveguide path.

A sensor according to the ninth aspect of the invention measures a propagation characteristic of a surface acoustic wave in a surface acoustic wave element, and light waveguided through an interior of the surface acoustic wave element.

A sensor according to the tenth aspect of the invention comprises:

a crystal oscillator or a surface acoustic wave element; and a metallic colloid layer formed on the crystal oscillator or the surface acoustic wave element.

The sensor of the invention is provided with a sensitive material layer whose optical characteristic is changed by substance adsorption.

The Effect of the Invention

The substance adsorption detection method and the sensor of the invention facilitate detection and identification of a substance to be detected by utilizing a change in outgoing light originating from a change in propagation loss and a change in the oscillation characteristic of the crystal oscillator, both caused by adsorption of the detection target substance on the surface of the core of the optical waveguide path. For example, in a case where substances other than the detection target substance are adsorbed at the same time, adsorption of different media which are impossible to identify merely with the oscillation characteristic of the crystal oscillator of the sensor can be detected by simultaneous measurement of refractive indices because of changes in optical characteristics.

The crystal and the electrode can respectively function as a clad and a core by using, as the electrode, the transparent conductive material whose refractive index is sufficiently larger than that of the crystal. Further, the crystal can function as a core.

As the metallic thin film is provided on the core, surface plasmons on the metallic thin film can be resonantly excited by an evanescent wave generated in the vicinity of the core by waveguided light. As the surface plasmon is excited, the waveguided light is attenuated, and the excitation condition is sensitively changed by adsorption of a substance. This makes it possible to observe the oscillation characteristic of the crystal oscillator while measuring the optical characteristic with a higher sensitivity by measuring outgoing light. Further, with deposition of a sensitive material whose optical characteristic is changed by adsorption of the substance on the surface of the metallic thin film, a trace of the substance can be detected more accurately.

Further, the provision of the optical waveguide in or on the surface elastic wave element makes it possible to observe light propagated through the waveguide path while measuring the propagation characteristic of a surface elastic wave. This makes it possible to detect adsorption of a substance.

Further, it is possible to measure a change in transmitted light or scattered light originating from adsorption of a substance by utilizing the characteristic of a metallic colloid which generates a local plasmon (LP) when irradiated with light.

As the sensitive material whose optical characteristic changes due to adsorption of a substance to be detected, thereby changing the propagation loss significantly, is deposited on the top layer, a trace of a substance can be detected accurately.

The substance adsorption detection method and the sensor of the invention can detect the adsorbed mass of a substance by the piezoelectric element (crystal oscillator or surface elastic wave element) having an optical waveguide path, and observe the optical characteristics of the adsorbed substance and the detection thin film after adsorption of the substance from a change in outgoing light caused by adsorption of the substance.

The foregoing method can accurately detect the amount of a change in adsorbed mass and the amount of a change in optical characteristic in comparison with a case where measurement is performed with a piezoelectric element and an element for measuring the optical characteristic prepared separately. Particularly, in a case where light irradiation causes decomposition of an adsorbed substance, or accelerates adsorption or desorption, separate preparation of the elements causes a large error, but integrating them makes it possible to measure such a photodecomposition and a light-oriented adsorption phenomenon in detail.

It is possible to identify substances having different masses which give the same change in optical physical property per, for example, the number of adsorption molecules by observing relationships between adsorbed masses and optical characteristics of some substances to be detected.

BEST MODE FOR CARRYING OUT THE INVENTION

Each of preferred embodiments of a substance adsorption detection method and a sensor using the method according to the invention will be explained with reference to the accompanying drawings. In the embodiments, the same structural parts will be denoted by the same reference symbols to omit the redundant explanation of the common parts as much as possible.

According to the invention, a crystal oscillator having an optical waveguide path is constituted, and the oscillation characteristic of the crystal oscillator and light emitted from the waveguide path are simultaneously and alternately observed.

FIRST EMBODIMENT

Figure 1:
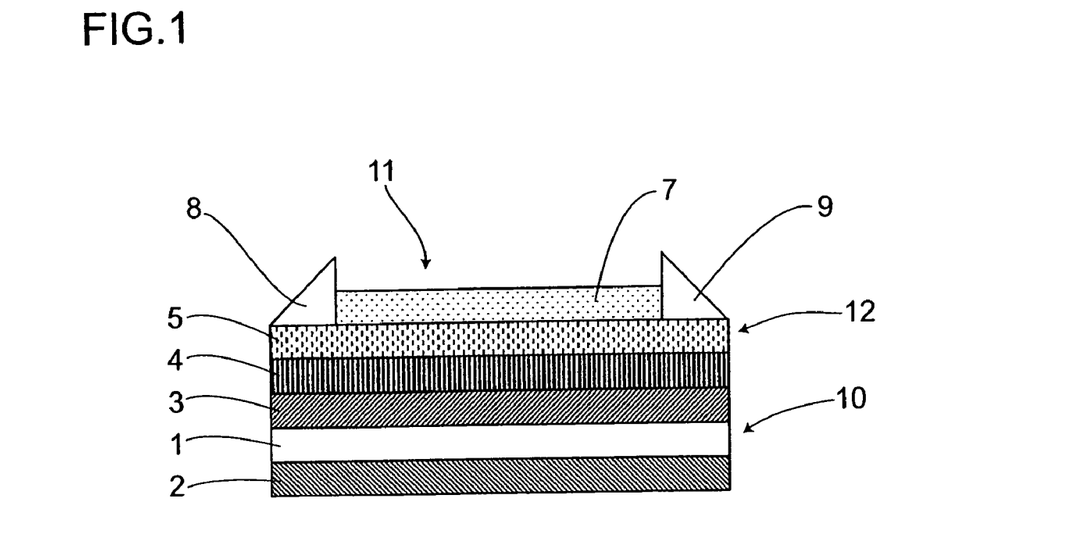
FIG. 1 is a longitudinal cross-sectional view illustrating the structure of a sensor according to a first embodiment of the invention.

FIG. 1 illustrates the arrangement example of the sensor according to the invention, and the sensor comprises a crystal oscillator 10 which has a crystal 1 and a pair of electrodes 2, 3 for crystal oscillation, an optical waveguide layer 12 which has a clad 4 made of a relatively low refractive index medium on the crystal oscillation electrode 3, and a core 5 made of a relatively high refractive index medium disposed on the clad 4, a gas adsorption member 11 which has a thin film 7 for detecting an adsorption substance and is disposed on the optical waveguide layer 12, an incoming light prism 8 which is light inputting means for allowing light to enter the core 5, and an outgoing light prism 9 which is light emitting means for acquiring light from the core 5. In the sensor element, the adsorbed-substance detecting thin film 7 is formed of an organic functional substance like porphyrin, and any material which adsorbs a substance to be detected, and changes its optical characteristic (complex dielectric constant) with, adsorption may be used for the thin film 7, which may be omitted.

The clad 4 of the low refractive index medium enables light waveguiding at the core 5. The core 5 is made of a medium which has a higher refractive index than that of the surroundings where the clad 4 and the element are revealed. The clad 4 and the core 5 may be made of any material which enables light waveguiding. As light enters the core 5, the light is waveguided while being reflected totally. At this time, a change in outgoing light from the core 5 originating from adsorption of the detection target substance is observed. The crystal oscillator 10 can detect the amount of adsorption of the adsorbed substance.

Next, the action of the invention will be explained.

The sensor element is exposed to the detection target substance during which a change in the oscillation frequency of the crystal oscillator 10 is observed. At the same time, light is input to the core 5 through the incoming light prism 8 from a light source (not illustrated), and waveguided. A light incident angle is set to an angle within a range where light is reflected totally and waveguided in the core 5. As light is waveguided in the core 5, an evanescent field is generated in the vicinity of the surface of the core on the exterior thereof (this distance is determined based on the dielectric constant of an interfacial medium and the incident angle). If a light absorptive substance is present in the area where the evanescent field is generated, the evanescent field is absorbed, so that the light which is waveguided through the core 5 is attenuated. The adsorbed-substance detecting thin film 7 is present within an area where an evanescent wave penetrates. As the light absorption characteristic of the adsorbed-substance detecting thin film 7 which has adsorbed the detection target substance is changed from the light absorption characteristic before adsorption, absorption of the evanescent wave by the adsorbed-substance detecting thin film 7 changes, so that the state of attenuation of light emitted from the core 5 through the outgoing light prism 9 changes. Outgoing light is measured by a light detector (not illustrated). If the detection target substance itself is light absorptive, the adsorbed-substance detecting thin film 7 need not be light absorptive. If the refractive index of the adsorbed-substance detecting thin film 7 becomes larger than that of the core 5, the light leaks from the core 5, but by utilizing this phenomenon, a substance that changes its refractive index through adsorption of the detection target substance and can change the outgoing light by the optical confinement and changing the propagation loss in the core 5, may be used as the adsorbed-substance detecting thin film 7. It is to be noted that incoming light is white light or monochromatic light absorbed by the adsorbed-substance detecting thin film 7 or the detection target substance and including a wavelength which causes the propagation loss to be changed by adsorption of the detection target substance, thereby changing the outgoing light intensity. As the detection target substance is adsorbed on the surface of the element, thus the surface of the adsorbed-substance detecting thin film 7, the spectrum or the intensity of light emitted from the core 5 changes because of the foregoing reason. At this time, the mass of the sensor element increases by what corresponds to the amount of adsorption of the detection target substance. Because the crystal oscillator 10 has a characteristic (QCM) of changing the unique oscillation frequency in accordance with the mass of the deposit adhered to the surface of the crystal oscillator 10, the frequency decreases as the amount of adsorption of a gas to be detected increases. That is, the frequency characteristic of the crystal oscillator 10 changes substantially in proportion to the mass of the adsorbed detection target gas. Because the outgoing light characteristic and the frequency characteristic indicate unique values in accordance with the adsorbed amount and the kind of the detection target substance, the detection target substance is detected and identified by comparing the relationship between changes in adsorbed mass and changes in light transmittance characteristics of some detection target substances observed beforehand. In this manner, it is possible to detect and identify the detection target substance based on the adsorbed amount of the detection target substance, i.e., the amount of a change in outgoing light corresponding to the frequency change of the crystal oscillator 10.

As explained above, the substance adsorption detection method of the embodiment provides the optical waveguide layer 11 comprising the clad 4 made of a relatively low refractive index medium and the core 5 made of a relatively high refractive index medium stacked on the crystal oscillator 10, and measures the oscillation characteristic of the crystal oscillator 10 and light waveguided with the optical waveguide layer serving as the optical waveguide path.

The sensor of the embodiment is structured in such a manner as to stack the clad 4 made of a relatively low reflective index medium and the core 5 made of a relatively relatively high reflective index medium on the crystal oscillator, and is provided with the optical waveguide layer 11 to be an optical waveguide path where light is waveguided.

The aforementioned structure facilitates detection and identification of a detection target substance by utilizing a change in outgoing light and a change in the oscillation frequency of the crystal oscillator 10, both originating from a change in the propagation loss as the detection target substance is adsorbed on the surface of the core 5 of the optical waveguide layer 11. For example, in a case where a medium other than the detection target substance is adsorbed together with the detection target substance, it is impossible to identify them only with the oscillation characteristic of the crystal oscillator 10 of the sensor, while it is possible to detect that the different medium is adsorbed by simultaneously performing refractive index measurement based on a change in the optical characteristic.

Further, as the sensitive material whose optical characteristic is changed by adsorption of the detection target substance, thereby changing the propagation loss significantly, is deposited on the surface of the core 5 located in the uppermost layer of the sensor, a trace of a substance on the surface of the core 5 can be detected.

It is possible to detect the adsorbed amount of the substance by the oscillation frequency characteristic of the crystal oscillator 10, and it is possible to observe the optical characteristics of the adsorbed substance or the thin film 7 for detection after adsorption of the substance, from the change in the outgoing light caused by the adsorption of the substance by a single element.

In comparison with a case where observation is performed with the crystal oscillator 10 and an element for measuring the optical characteristic separately prepared, the foregoing method can accurately detect the amount of a change in adsorbed mass and the amount of a change in optical characteristic. Particularly, in a case where light irradiation causes decomposition of an adsorbed substance, or accelerates adsorption or desorption, if the QCM and the optical waveguide path are prepared separately from each other, this causes a large error, but integrating them makes it possible to measure such a photodecomposition and a light-oriented adsorption phenomenon in detail.

It is possible to identify substances having different masses which give the same change in optical physical property per, for example, the number of adsorption molecules by observing the relationships between adsorbed masses and optical characteristics of some substances to be detected beforehand.

Another structure of the sensor of the embodiment is characterized by having the crystal oscillator 10 that comprises the crystal 1, the electrode 2 formed on one side of the crystal 1, and the electrode 3 as an optical waveguide electrode which is formed on the other side of the crystal 1, made of a transparent conductive material having a higher refractive index than that of the crystal 1, and serves as an optical waveguide path where light is waveguided.

According to the structure, the use of the transparent conductive material having a sufficiently larger refractive index than that of the crystal 1 as the electrode 3, and permission of light to enter the electrode 3 makes it possible to allow the crystal 1 and the electrode 3 to function as a clad and a core respectively.

A further structure of the sensor of the embodiment is characterized by allowing the crystal 1, or the crystal 1, the electrode 2, and the electrode 3 to work as an optical waveguide path in the crystal oscillator 10 comprising the crystal 1, and the electrodes 2, 3 formed on the respective sides of the crystal 1.

According to the structure, as light enters the crystal 1, the crystal 1 can function as a core when the electrode 2 and the electrode 3 are made of metallic thin films, or when the electrode 2 and the electrode 3 are made of transparent media and the refractive index of the crystal 1 is larger than those of the electrode 2 and the electrode 3, and a portion extending from the electrode 2 through the crystal 1 to the electrode 3 can function as a core when the electrode 2 and the electrode 3 are made of transparent media and the refractive index of the crystal 1 is smaller than those of the electrode 2 and the electrode 3.

SECOND EMBODIMENT

Figure 2:
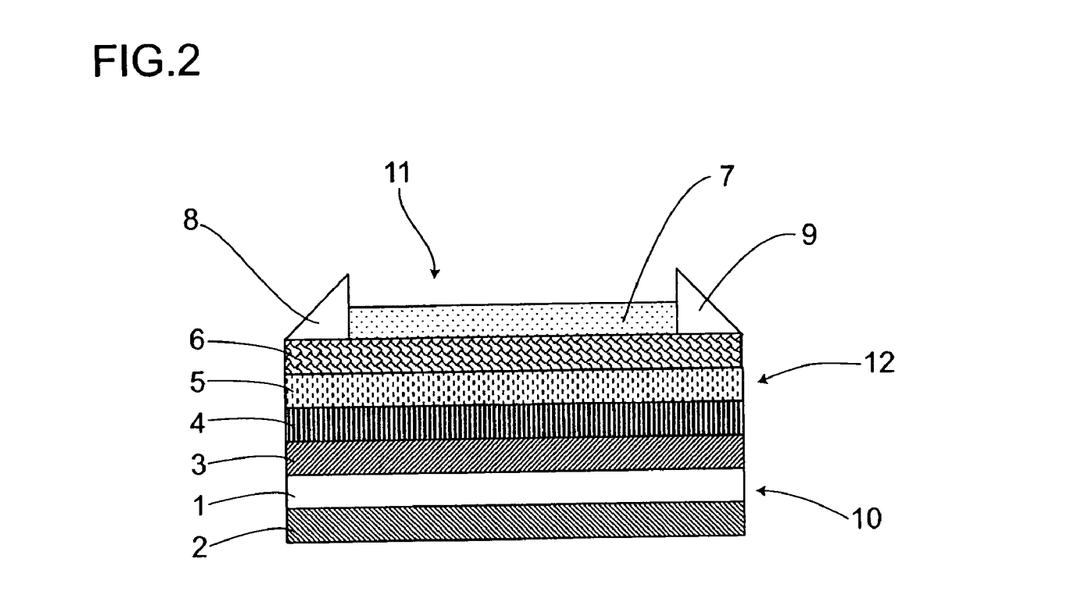
FIG. 2 is a longitudinal cross-sectional view illustrating the structure of a sensor according to a second embodiment of the invention.

Next, the second embodiment will be explained. In the embodiment, as illustrated in FIG. 2, a metallic thin film 6 having an appropriate thickness is disposed between the core 5 and the adsorbed-substance detecting thin film 7. In this case, a surface plasmon can be excited on the surface of the metallic thin film with respect to a wavelength and an incident angle determined by the thicknesses and dielectric constants of the core 5 and the metallic thin film 6, the thickness and dielectric constant of the adsorbed-substance detecting thin film 7, and the dielectric constant of surroundings. At this time, transmitted light is attenuated at a wavelength at which the surface plasmon is excited. The dielectric constant or the thickness of the absorption substance detection thin film 7 after absorption of the detection target substance is obtained by performing theoretical computation of the amount of attenuation of transmitted light, and the state of oscillation of the crystal oscillator 10 is detected. In this case, the adsorption detection thin film and the detection target substance need not be light absorptive.

As explained above, the substance adsorption detection method of the embodiment is characterized by providing the metallic thin film 6 on the core 5. The sensor of the invention is having the metallic thin film 6 provided on the core 5.

According to the foregoing structure, because of the metallic thin film 6 provided on the core 5, surface plasmons in the metallic surface 6 can be resonantly excited by an evanescent wave generated in the vicinity of the core 5 by waveguided light. As the surface plasmons are excited, the waveguided light is attenuated, and the excitation condition is sensitively changed by adsorption of a substance. This makes it possible to observe the oscillation characteristic of the crystal oscillator 10 while observing the optical characteristic sensitively by observing outgoing light.

Further, with deposition of a sensitive material whose optical characteristic is changed by adsorption of the substance on the surface of the metallic thin film 6, the trace of substance can be detected more accurately.

THIRD EMBODIMENT

Recently, there is proposed a sensor using a local plasmon (LP) which is generated when a metallic colloid whose diameter is about several tens of nm is irradiated with light. This utilizes that the resonance wavelength and light absorption intensity, or the light scattering intensity of the LP changes depending on the refractive index of a substance and the film thickness thereof when the substance is adsorbed on the surface of the metallic colloid.

Figure 3:
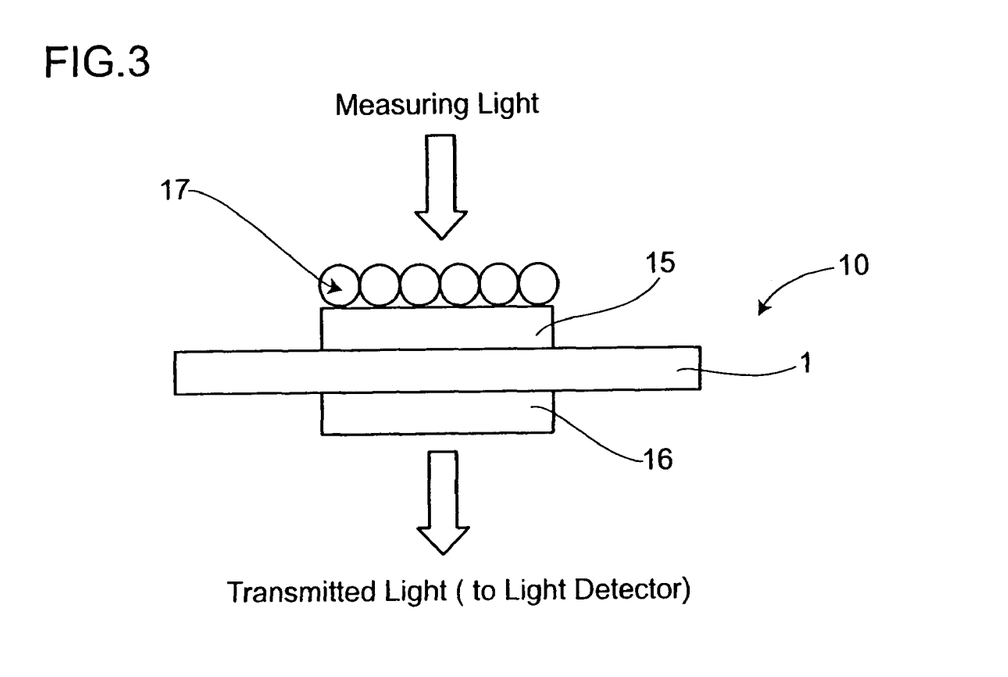
FIG. 3 is a longitudinal cross-sectional view illustrating the structure of a sensor according to a third embodiment of the invention.

In the embodiment, the metallic colloid is deposited on the crystal oscillator 10, and an optical change and a change in mass both originating from adsorption of a substance are measured in a complex manner with each other by simultaneously measuring the resonance wavelength of the LP and a change in the oscillation frequency of the crystal oscillator 10. FIG. 3 illustrates a structural example. Gold (Au) colloids 17 as a metallic colloid layer are deposited on the crystal oscillator 10 having the crystal 1 sandwiched between a pair of electrodes 15, 16. The detection target substance is adsorbed on the gold colloids 17, a change in mass is observed by the crystal oscillator 10, and the resonance wavelength (absorption peak wavelength) of the LP in the gold colloids 17 and the refractive index of the adsorbed substance are observed by measuring transmitted light or scattered light. At this time, if the electrodes 15, 16 are transparent, transmitted light of the gold colloid thin film on the electrode can be observed. If the electrodes 15, 16 are not transparent, transmitted light of the gold colloid thin film in the vicinity of the electrode is observed.

As explained above, the sensor of the embodiment has the crystal oscillator 10 comprising the crystal 1 and the electrodes 15, 16, and the gold colloids 17 as the metallic colloid layer formed on the crystal oscillator 10.

The foregoing structure enables measurement of a change in transmitted light originating from the adsorption of the substance by utilizing the characteristic of the gold colloids 17 which generate the local plasmon (LP) when irradiated with light. At this time, scattered light may be used for light detection. Note that a surface elastic wave element may be used as mass detection means.

FOURTH EMBODIMENT

Figure 4:
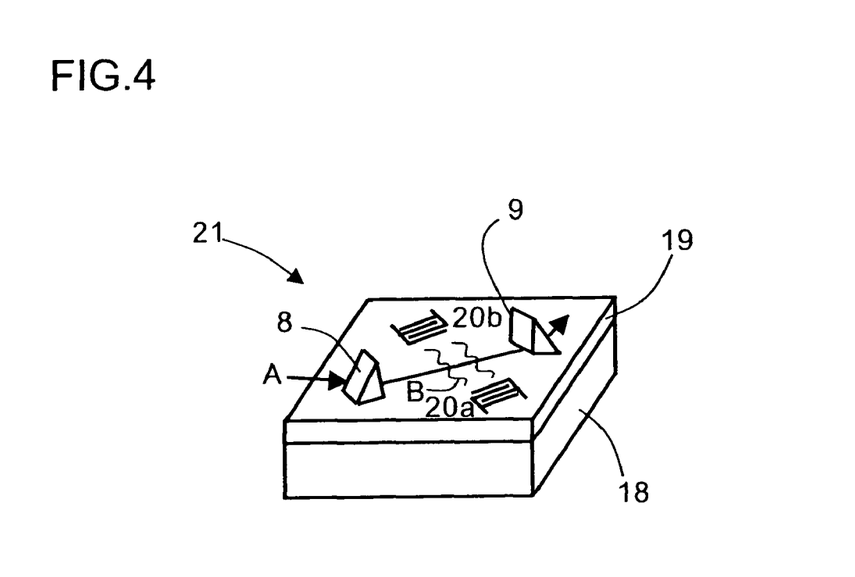
FIG. 4 is a perspective view illustrating the structure of a sensor according to a fourth embodiment of the invention.

Next, the fourth embodiment will be explained. As illustrated in FIG. 4, the embodiment comprises a surface elastic wave element 21 which comprises a piezoelectric element 19 on a low refractive index substrate 18, and comb-like opposing electrodes 20a, 20b, the incoming light prism 8 and the outgoing light prism 9. The refractive index of the piezoelectric element 19 is set larger than that of the substrate 18, so that the piezoelectric element 19 functions as an optical waveguide path. When a substance is adsorbed on the piezoelectric element 19, waveguided light A which propagates in the optical waveguide path is observed while the propagation characteristic of a surface elastic wave B is measured by the electrodes 20a, 20b. It is possible to employ a structure such that another optical waveguide path or a sensitive material surface whose optical characteristic is changed by substance adsorption is stacked on the piezoelectric element 19. The main operation is the same as that of the first embodiment.

According to the sensor of the embodiment, a single sensor element can detect the adsorbed mass of the substance based on the oscillation frequency of the crystal oscillator 10 or the surface elastic wave element 21, and the amount of a change in outgoing light characteristic with respect to the adsorbed mass can be observed. This makes the conventional use of two aligned sensors unnecessary, thus ensuring pinpoint and accurate detection of a point (spot) to be a detection target.

In the foregoing embodiments, the sensor may be located in a gas or in a liquid.

The invention is not limited to the foregoing embodiments, and can be modified without departing from the spirit of the invention. The shape of the adsorbed-substance detecting thin film 7 is in no way restrictive, and it is possible to detect various substances by changing materials.

INDUSTRIAL APPLICABILITY

A possible application example of the embodiment is detection and identification of an oxidizing gas like nitrogen oxide in a gas, a basic gas like ammonia, an organic solvent gas, a biogenic substance in a liquid, and the like by selecting a substance for detecting an adsorbed substance. It is expected that the invention can be applied to an environmental monitor and process management.

What is claimed is:

1. A substance adsorption detection method using the sensor having a crystal oscillator, the method comprising:
   providing a sensor with an optical waveguide path disposed on the crystal oscillator, said crystal oscillator comprising a crystal and electrodes formed on either face of said crystal, wherein said optical waveguide path is an optical waveguide layer which has a clad portion and a core arranged on said clad portion, said core being made of a higher refractive index medium than said clad portion, both said core and said clad portion being stacked on said crystal oscillator;
   providing light inputting means and light emitting means positioned on end portions of said optical waveguide path on which a detection target substance is adsorbed, wherein said light inputting means for allowing light to enter said core is provided on one end portion thereof and said light emitting means for acquiring light from said core is provided on the other end portion thereof;
   exposing said sensor to said detection target substance, while inputting light through said light inputting means to said core of the optical waveguide path; and
   measuring an oscillation characteristic of said crystal oscillator and light transmitted on said optical waveguide path through said core while the light is repeatedly reflected in said core, said light being emitted through said light emitting means.

2. The substance adsorption detection method according to claim 1, wherein a metallic film is formed on said optical waveguide path and a thin film is further provided to adsorb a detection target substance thereon, said thin film being a sensitive material layer whose optical characteristic is changed by substance adsorption.

3. The substance adsorption detection method comprising:
   providing a sensor with a crystal oscillator, said crystal oscillator comprising a crystal and electrodes formed on either face of said crystal, wherein at least one of said electrodes is made of an electrically conductive transparent material having a higher refractive index than that of the crystal, and wherein said crystal oscillator serves as an optical waveguide path made of a clad portion of said crystal and a core of said transparent conductive material electrodes, or made of a stacked core of said crystal and said transparent conductive material electrodes;
   providing light inputting means and light emitting means positioned on end portions of said optical waveguide path on which a detection target substance is adsorbed, wherein said light inputting means for allowing light to enter said core is provided on one end portion thereof and said light emitting means for acquiring light from said core is provided on the other end portion thereof;
   exposing said sensor to said detection target substance, while inputting light through said light inputting means to said core of the optical waveguide path; and
   measuring an oscillation characteristic of said crystal oscillator and light transmitted on said optical waveguide path through said core while the light is repeatedly reflected in said core, said light being emitted through said light emitting means.

4. The substance adsorption detection method according to claim 3, wherein a metallic film is formed on said optical waveguide path and a thin film is further provided to adsorb a detection target substance thereon, said thin film being a sensitive material layer whose optical characteristic is changed by substance adsorption.

5. The substance adsorption detection method comprising:
   providing a sensor with a crystal oscillator, said crystal oscillator comprising a crystal and electrodes formed on either face of said crystal, wherein at least one of said electrodes is a clad portion made of an electrically conductive transparent material having a lower refractive index than that of the crystal, and wherein said crystal oscillator serves as an optical waveguide path made of a core of said crystal;
   providing light inputting means and light emitting means positioned on end portions of said optical waveguide path on which a detection target substance is adsorbed, wherein said light inputting means for allowing light to enter said core is provided on one end portion thereof and said light emitting means for acquiring light from said core is provided on the other end portion thereof;
   exposing said sensor to said detection target substance, while inputting light through said light inputting means to said core of the optical waveguide path; and
   measuring an oscillation characteristic of said crystal oscillator and light transmitted on said optical waveguide path through said core while the light is repeatedly reflected in said core, said light being emitted through said light emitting means.

6. The substance adsorption detection method according to claim 5, wherein a metallic film is formed on said optical waveguide path and a thin film is further provided to adsorb a detection target substance thereon, said thin film being a sensitive material layer whose optical characteristic is changed by substance adsorption.

7. The substance adsorption detection method according to any one of claims 1, 3, and 5, wherein a metallic film is formed on said optical waveguide path.

8. The substance adsorption detection method according to any one of claims 1, 3 and 5, further comprising a thin film on which a detection target substance is adsorbed, said thin film being a sensitive material layer whose optical characteristic is changed by substance adsorption.

9. A substance adsorption detection method comprising:
providing a sensor with a surface acoustic wave element, said surface acoustic wave element comprising a piezoelectric element on a substrate and comb-like opposing electrodes, wherein said piezoelectric element has a higher refractive index than that of said substrate, and wherein said surface acoustic wave element serves as an optical waveguide path made of a clad portion of said substrate and a core of said piezoelectric element;
providing light inputting means and light emitting means positioned on either end portion of said core, wherein said light inputting means for allowing light to enter said core is provided on one end portion thereof and said light emitting means for acquiring light from said core is provided on the other end portion thereof;
inputting light through said light inputting means to said core of the optical waveguide path while a detection target substance adsorbs on said piezoelectric element; and
measuring a propagation characteristic of said surface acoustic wave by said comb-like opposing electrodes in said surface acoustic wave element, and light guided through said core of said optical waveguide path provided in said surface acoustic wave element while the light is repeatedly reflected in said core, said light being emitted through said light emitting means.

10. The substance absorption detection method according to claim 9, wherein a thin film on which a detection target substance is adsorbed is provided on said piezoelectric element, and said thin film is a sensitive material layer whose optical characteristic is changed by substance adsorption.

11. A sensor having a crystal oscillator, the sensor comprising:
said crystal oscillator comprising a crystal and electrodes formed on either face of said crystal; and
an optical waveguide path disposed on the crystal oscillator, wherein said optical wave guide path is an optical wave guide layer which has a clad portion and a core arranged on said clad portion, said core being made of a higher refractive index medium than said clad portion, both said core and said clad portion being stacked on said crystal oscillator;
wherein light inputting means and light emitting means are provided on end portions of said optical waveguide path on which a detection target substance is adsorbed, said light inputting means for allowing light to enter said core being provided on one end portion thereof and said light emitting means for acquiring light from said core being provided on the other end portion thereof,
wherein said sensor is exposed to said detection target substance, while inputting light through said light inputting means to said core of the optical waveguide path; and
wherein said sensor measures an oscillation characteristic of said crystal oscillator and light transmitted on said optical waveguide path through said core while the light is repeatedly reflected in said core, said light being emitted through said light emitting means.

12. The sensor according to claim 11, wherein a metallic film is formed on said optical wave guide path and a thin film on which a detection target substance is adsorbed is further provided, said thin film being a sensitive material layer whose optical characteristic is changed by substance adsorption.

13. A sensor comprising:
a crystal oscillator comprising a crystal and electrodes formed on either face of said crystal, wherein at least one of said electrodes is made of an electrically conductive transparent material having a higher refractive index than that of the crystal, and wherein said crystal oscillator serves as an optical waveguide path made of a clad portion of said crystal and a core of said transparent conductive material electrodes, or made of a stacked core of said crystal and said transparent conductive material electrodes;
wherein light inputting means and light emitting means are provided on end portions of said optical waveguide path on which a detection target substance is adsorbed, said light inputting means for allowing light to enter said core being provided on one end portion thereof and said light emitting means for acquiring light from said core being provided on the other end portion thereof;
wherein said sensor is exposed to said detection target substance, while inputting light through said light inputting means to said core of the optical waveguide path; and
wherein said sensor measures an oscillation characteristic of said crystal oscillator and light transmitted on said optical waveguide path through said core while the light is repeatedly reflected in said core, said light being emitted through said light emitting means.

14. The sensor according to claim 13, wherein a metallic film is formed on said optical waveguide path and a thin film on which a detection target substance is adsorbed is further provided, said thin film being a sensitive material layer whose optical characteristic is changed by substance adsorption.

15. A sensor comprising:
a crystal oscillator comprising a crystal and electrodes formed on either face of said crystal, wherein at least one of said electrodes is a clad portion made of an electrically conductive transparent material having a lower refractive index than that of the crystal, and wherein said crystal oscillator serves as an optical waveguide path made of a core of said crystal;
wherein light inputting means and light emitting means are provided on end portions of said optical waveguide path on which a detection target substance is adsorbed, said light inputting means for allowing light to enter said core being provided on one end portion thereof and said light emitting means for acquiring light from said core being provided on the other end portion thereof;
wherein said sensor is exposed to said detection target substance, while inputting light through said light inputting means to said core of the optical waveguide path; and
wherein said sensor measures an oscillation characteristic of said crystal oscillator and light transmitted on said optical waveguide path through said core while the light is repeatedly reflected in said core, said light being emitted through said light emitting means.

16. The sensor according to claim 15, wherein a metallic film is formed on said optical waveguide path and a thin film on which a detection target substance is adsorbed is further provided, said thin film being a sensitive material layer whose optical characteristic is changed by substance adsorption.

17. The sensor according to any one of claims 11, 13 and 15, wherein a metallic film is formed on said optical waveguide path.

18. The sensor according to any one of claims 11, 13 and 15, further comprising a thin film on which a detection target substance is adsorbed, said thin film being a sensitive material layer whose optical characteristic is changed by substance adsorption.

19. A sensor comprising:
a surface acoustic wave element comprising a piezoelectric element on a substrate and comb-like opposing electrodes, wherein said piezoelectric element has a higher refractive index than that of said substrate, and wherein said surface acoustic wave element serves as an optical waveguide path made of a clad portion of said substrate and a core of said piezoelectric element;
wherein light inputting means and light emitting means are provided on either end portion of said core, wherein said light inputting means for allowing light to enter said core is provided on one end portion thereof and said light emitting means for acquiring light from said core is provided on the other end portion thereof;
wherein light is input through said light inputting means to said core of the optical waveguide path while a detection target substance adsorbs on said piezoelectric element; and
wherein said sensor measures a propagation characteristic of said surface acoustic wave by said comb-like opposing electrodes in said surface acoustic wave element, and light guided through said core of said optical waveguide path provided in said surface acoustic wave element while the light is repeatedly reflected in said core, said light being emitted through said light emitting means.

20. The sensor according to claim 19, wherein a thin film on which a detection target substance is adsorbed is provided on said piezoelectric element, and said thin film is a sensitive material layer whose optical characteristic is changed by substance adsorption.

21. A substance adsorption detection method comprising:
providing a sensor with a crystal oscillator, said crystal oscillator comprising a crystal and electrodes formed on either face of said crystal, wherein at least one of said electrodes is made of a metallic thin film, and wherein said crystal oscillator serves as an optical waveguide path made of a core of said crystal;
providing light inputting means and light emitting means positioned on end portions of said optical waveguide path on which a detection target substance is adsorbed, wherein said light inputting means for allowing light to enter said core is provided on one end portion thereof and said light emitting means for acquiring light from said core is provided on the other end portion thereof;
exposing said sensor to said detection target substance, while inputting light through said light inputting means to said core of the optical waveguide path; and
measuring an oscillation characteristic of said crystal oscillator and light transmitted on said optical waveguide path through said core while the light is repeatedly reflected in said core, said light being emitted through said light emitting means.

22. The substance absorption detection method according to claim 21, further comprising a thin film provided on said metallic electrode, said detection target substance being adsorbed on said thin film.

23. A sensor comprising:
a crystal oscillator comprising a crystal and electrodes formed on either face of said crystal, wherein at least one of said electrodes is made of a metallic thin film, and wherein said crystal oscillator serves as an optical waveguide path made of a core of said crystal;
wherein light inputting means and light emitting means are provided on end portions of said optical waveguide path on which a detection target substance is adsorbed, said light inputting means for allowing light to enter said core being provided on one end portion thereof and said light emitting means for acquiring light from said core being provided on the other end portion thereof;
wherein said sensor is exposed to said detection target substance, while inputting light through said light inputting means to said core of the optical waveguide path; and
wherein said sensor measures an oscillation characteristic of said crystal oscillator and light transmitted on said optical waveguide path through said core while the light is repeatedly reflected in said core, said light being emitted through said light emitting means.

24. The sensor according to claim 23, further comprising a thin film provided on said metallic electrode, said detection target substance being adsorbed on said thin film.

* * * * *